(12) United States Patent
Kim et al.

(10) Patent No.: US 9,518,233 B2
(45) Date of Patent: Dec. 13, 2016

(54) CATALYST FOR A HYDRODGENATION DEWAXING PROCESS AND METHOD FOR MANUFACTURING SAME

(71) Applicant: SK Innovation Co., Ltd., Seoul (KR)

(72) Inventors: Tae Jin Kim, Daejeon (KR); Seung Woo Lee, Daejeon (KR); Yoon Kyung Lee, Chungcheongbuk-do (KR); Seung Hoon Oh, Seoul (KR); Jae Suk Choi, Seoul (KR)

(73) Assignee: SK INNOVATION CO., LTD., Seoul (KR)

( * ) Notice: Subject to any disclaimer, the term of this patent is extended or adjusted under 35 U.S.C. 154(b) by 269 days.

(21) Appl. No.: 14/306,447

(22) Filed: Jun. 17, 2014

(65) Prior Publication Data

US 2014/0367310 A1     Dec. 18, 2014

Related U.S. Application Data

(62) Division of application No. 13/640,788, filed as application No. PCT/KR2011/002054 on Mar. 25, 2011, now Pat. No. 8,772,193.

(30) Foreign Application Priority Data

Apr. 14, 2010    (KR) ........................ 10-2010-0034451

(51) Int. Cl.

| | | |
|---|---|---|
| *C10G 47/00* | (2006.01) | |
| *C10G 47/16* | (2006.01) | |
| *B01J 29/72* | (2006.01) | |
| *B01J 29/74* | (2006.01) | |
| *C10G 45/62* | (2006.01) | |
| *C10G 45/64* | (2006.01) | |
| *B01J 35/10* | (2006.01) | |
| *C07C 5/27* | (2006.01) | |
| *C01B 39/48* | (2006.01) | |
| *C07C 9/22* | (2006.01) | |
| *B01J 35/00* | (2006.01) | |

(52) U.S. Cl.
CPC ............... *C10G 47/16* (2013.01); *B01J 29/72* (2013.01); *B01J 29/74* (2013.01); *B01J 35/002* (2013.01); *B01J 35/1019* (2013.01); *C01B 39/48* (2013.01); *C07C 5/2775* (2013.01); *C10G 45/62* (2013.01); *C10G 45/64* (2013.01); *B01J 35/006* (2013.01); *B01J 2229/20* (2013.01); *B01J 2229/42* (2013.01); *C07C 9/22* (2013.01); *C07C 2523/42* (2013.01); *C07C 2523/44* (2013.01); *C07C 2523/58* (2013.01); *C07C 2529/74* (2013.01); *C10G 2300/4018* (2013.01); *C10G 2400/02* (2013.01); *C10G 2400/04* (2013.01); *C10G 2400/10* (2013.01); *Y02P 20/52* (2015.11)

(58) Field of Classification Search
USPC ..................................... 208/111.01, 135, 137
See application file for complete search history.

(56) References Cited

U.S. PATENT DOCUMENTS

| | | | |
|---|---|---|---|
| 4,741,891 A | 5/1988 | Casci et al. | |
| 5,128,024 A | 7/1992 | LaPierre et al. | |
| 6,514,479 B1 | 2/2003 | Merlen et al. | |
| 7,482,300 B2 | 1/2009 | Lai et al. | |
| 8,772,193 B2 | 7/2014 | Kim et al. | |

FOREIGN PATENT DOCUMENTS

| | | |
|---|---|---|
| KR | 1019910001498 | 3/1991 |
| KR | 100199849 | 6/1999 |
| KR | 100404500 | 2/2004 |
| KR | 100851143 | 8/2008 |

OTHER PUBLICATIONS

International Search Report of International Application No. PCT/KR2011/002054 dated Nov. 30, 2011.

*Primary Examiner* — Elizabeth Wood
(74) *Attorney, Agent, or Firm* — Abelman, Frayne & Schwab

(57) ABSTRACT

The present invention relates to a bifunctional catalyst for a hydrodewaxing process with improved isomerization selectivity, and to a method for manufacturing the same, and more particularly to a bifunctional catalyst and to a method for manufacturing same, which is characterized in that EU-2 zeolite with a controlled degree of phase transformation is used as a catalyst support having an acid site. The EU-2 zeolite, the degree of phase transformation of which is controlled, includes, by controlling synthesis parameters of EU-2, predetermined amounts of materials that are phase-transformed from EU-2 crystals such as cristobalite and quartz. The metal loaded bifunctional catalyst according to the present invention improves selectivity of the isomerization process, rather than a cracking reaction, during a hydroisomerization reaction of n-hexadecane. Therefore, the bifunctional catalyst can be widely used as a catalyst for a dewaxing process such as lubricant base oil and diesel oil.

9 Claims, 2 Drawing Sheets

CATALYST FOR A HYDRODGENATION DEWAXING PROCESS AND METHOD FOR MANUFACTURING SAME

RELATED APPLICATIONS

This application is a Divisional Application of U.S. application Ser. No. 13/640,788 filed Oct. 12, 2012, now U.S. Pat. No. 8,772,193, which is a National Phase of PCT/KR2011/0022054, filed Mar. 25, 2011, which claims priority of Korean Application No. 10-2010-0034451, filed Apr. 14, 2010, the disclosures of which are incorporated herein by reference.

TECHNICAL FIELD

The present invention relates to a metal-containing bifunctional catalyst for a hydrodewaxing process and a method of manufacturing the same, and, more particularly, to a catalyst for a hydrodewaxing process, which is characterized in that EU-2 zeolite, the degree of phase transition thereof being controlled, is used as a catalyst support having an acid site, and to a method of manufacturing the same.

BACKGROUND ART

Recently, the hydroisomerization reaction of long-chain normal-paraffin has played an important part in an oil refining process. Long-chain normal-paraffin must be converted into iso-paraffin by a hydroisomerization reaction in order to improve cold flow properties at a low temperature and increase octane number. In particular, lately, the quality of a raw material has been deteriorated due to an increase in oil prices, whereas higher-quality fuel oil and lubricant products have been required due to the advancement of automobile engine technologies.

According to an example of the isomerization reaction used in an oil refining process, a C4 to C7 isomerized hydrocarbon can be applied to a process of manufacturing gasoline having a high octane number. The isomerization reaction of a C7 to C15 hydrocarbon can be practically used to manufacture high-grade diesel oil having a high cetane number and improved low-temperature cold flow properties. Further, the isomerization reaction of a normal C15 or more paraffin is put to practical use in the process of producing a high-grade lubricant having a high viscosity index. Particularly, since a commonly-used lubricant or jet oil needs low pour point and melting point, a technology for converting wax components using an isomerization reaction is required in order to produce a high-quality lubricant or jet oil. High boiling point, high molecular weight normal paraffins serving to increase the pour point coagulate to form a wax, and this wax must be removed for improving cold flow properties of the hydrocarbon feedstocks. Therefore, this hydroisomerization reaction for removing wax is referred to as "dewaxing". In the dewaxing process, a hydroisomerization reaction is accompanied by a hydrocracking reaction. The term "hydroisomerization" is used when hydroisomerization predominates over hydrocracking, whereas the term "hydrocracking" is used when hydrocracking predominates over hydroisomerization. In this case, in order to maximize the yield of a product, it is advantageous for normal-paraffin to be converted by hydroisomerization, not by hydrocracking.

It is reported that an hydroisomerization reaction is generally conducted with a bifunctional catalyst. A bifunctional catalyst is composed of two kinds of active compositions of a metal site for hydrogenation and dehydrogenation and a acidic support for skeletal isomerization generating carbenium ions. Therefore, such a catalyst is referred to as a bifunctional catalyst. The metal composition used in the bifunctional catalyst may be at least one selected from group VI metals and group VIII metals. Particularly, precious metals having high hydrogenation and dehydrogenation activity, such as platinum (Pt), palladium (Pd) and the like, may be chiefly used as the metal composition. The support used in the bifunctional catalyst may be selected from various materials having an acidic site, such as silica-alumina, clay, zeolite and the like. Particularly, zeolite can be advantageously used as an isomerization catalyst because it is structurally stable even under a severe reaction condition, has a large surface area and includes a number of acid sites.

In order to produce a bifunctional catalyst for optimizing isomerization and controlling cracking, many researches and patents for improving the performance of a dewaxing catalyst using a zeolite material having excellent shape selectivity have been disclosed. Particularly, it was reported that, among various kinds of zeolite materials, each of the zeolite materials (ZSM-22, ZSM-23, EU-2, ZSM-48 and the like) having a one-dimensional pore structure are used as a support of a catalyst having high selectivity to isomerization. Further, it is disclosed in U.S. Pat. No. 7,482,300 that the selectivity of ZSM-48 to isomerization can be improved when the purity of the crystal structure of ZSM-48 becomes high.

DISCLOSURE

Technical Problem

Accordingly, an object of the present invention is to provide a catalyst for a hydrodewaxing process, which has high selectivity to an isomerization reaction compared to conventional catalysts, and a method of manufacturing the catalyst.

Technical Solution

In order to accomplish the above object, an aspect of the present invention provides a method of manufacturing a catalyst for a hydrodewaxing process, including the steps of: (a) preparing an EU-2 zeolite support, the degree of phase transition of which is controlled such that a phase transition index (T) thereof is $50 \leq T < 100$; (b) metal loading on the EU-2 zeolite support for hydrogenation, the metal composition including at least one selected from the group consisting of group VI metals and group VIII metals; and (c) drying and calcinating the EU-2 zeolite support loaded with the metal composition, wherein <Formula 1> T=(TGA weight reduction rate of the synthesized EU-2 sample)/(TGA weight reduction rate of pure EU-2 reference sample)×100 (here, the TGA weight reduction rate of the EU-2 sample is measured under the condition that the sample is heated from 120° C. to 550° C. at a heating rate of 2° C./min and then maintained at 550° C. for 2 hours).

Another aspect of the present invention provides a catalyst for a hydrodewaxing process, including: an EU-2 zeolite support having an acid site, the phase transition index (T) thereof, represented by Formula 1 above, being $50 \leq T < 100$, and the molar ratio of silica and alumina thereof being 1 to 200; and a metal composition for hydrogenation loaded in the EU-2 zeolite support, the metal including at least one selected from the group consisting of group VI metals and group VIII metals.

Advantageous Effects

The bifunctional catalyst according to the present invention, in which EU-2 zeolite, the degree of phase transition thereof being controlled, is used as a support, exhibits improved selectivity to isomerization compared to conventional zeolite (ZSM-48, EU-2), and exhibits excellent performance even in the hydrodewaxing process. Therefore, the bifunctional catalyst can be used as a catalyst for a dewaxing process for producing a lubricant base oil. In addition, the bifunctional catalyst can be applied to a catalyst for manufacturing gasoline having a high octane number using an isomerization reaction of converting normal-paraffin into iso-paraffin using the bifunctional catalyst, and can be applied to a catalyst for improving the cold flow properties of diesel oil.

BEST MODE

Figure 1:
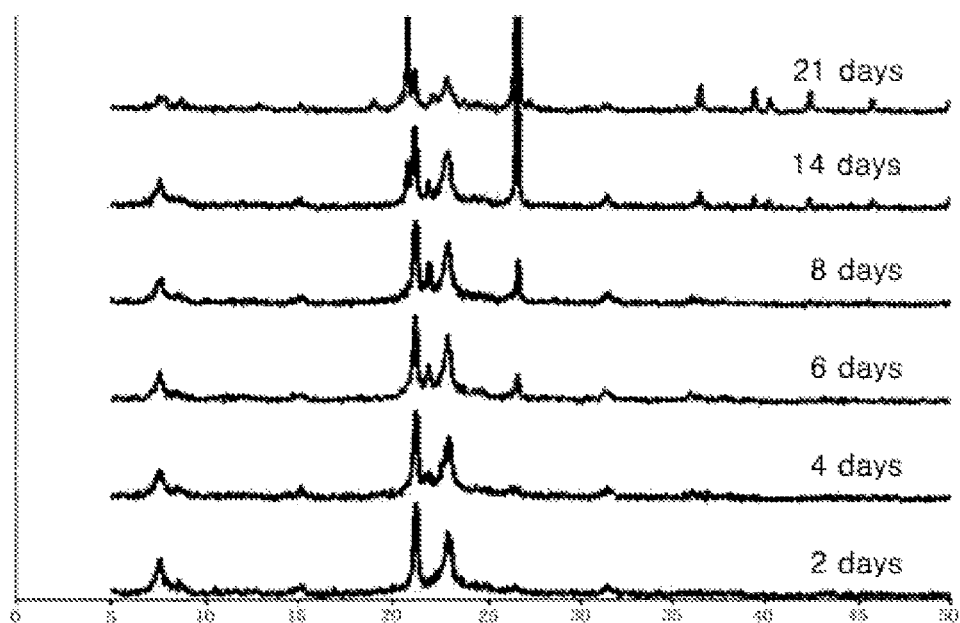
FIG. 1 is a view showing the X-ray diffraction (XRD) patterns of a hydrothermally-synthesized pure EU-2 zeolite material and an EU-2 zeolite material phase-transited with the passage of synthesis time.

The above and other objects, features and advantages of the present invention will be more clearly understood from the following detailed description taken in conjunction with the accompanying drawings, and thus the technical idea of the present invention will be embodied by those skilled in the art. Further, in the description of the present invention, when it is determined that the detailed description of the related art would obscure the gist of the present invention, the description thereof will be omitted.

Hereinafter, preferred embodiments of the present invention will be described in detail.

The present invention provides a method of using EU-2 zeolite, the degree of phase transition thereof being controlled, as a support of a dewaxing catalyst having high selectivity to an isomerization reaction. Most of conventional isomerization catalysts have used pure zeolite such as ZSM-48, EU-2 or the like. However, in the present invention, it was found that the efficiency of an isomerization reaction can be more improved according to the degree of phase transition of the zeolite. Therefore, the present invention can provide a catalyst material which can be optimized as a support of an isomerization catalyst by controlling the degree of phase transition of the zeolite.

The catalyst according to the present invention is characterized in that an EU-2 zeolite, the degree of phase transition of which is controlled such that its phase transition index (T) is 50~100 based on the reference EU-2 phase transition index proposed by the present researchers, is loaded with a metal composition for hydrogenation.

Generally, a zeolite material is prepared by mixing an organic template material with an aqueous alkali solution containing a silica raw material, an alumina raw material and the like and then hydrothermally synthesizing the mixture using a batch reactor such as an autoclave or the like. In this case, the characteristics such as structure, purity, crystal size and the like of the zeolite material depend on several variables, such as relative concentration between raw materials such as silica, alumina, alkali or alkali-earth metals, water and the like, whether aging is conducted before hydrothermal synthesis, hydrothermal synthesis temperature, hydrothermal synthesis time, whether stirring is conducted during hydrothermal synthesis, and the like. Particularly, in the process of hydrothermal synthesis of zeolite, pure zeolite having high crystallinity can be obtained only when a predetermined amount of time passes. However, when hydrothermal synthesis is continuously conducted even after pure zeolite is created, the pure zeolite is gradually transformed into a more stable phase with the passage of time.

EU-2 zeolite, which is a kind of zeolite used in a dewaxing catalyst, can be converted into pure EU-2 zeolite having high crystallinity after a predetermined amount of time when controlling hydrothermal synthesis conditions, but is gradually transformed into a stable phase when hydrothermal synthesis is continuously conducted. The phase occurring in this way may be cristobalite, quartz or the like. In this case, two or more phases or only one phase may occur according to the composition of raw materials and the synthesis time.

The present researchers found that, when EU-2 zeolites, the degree of phase transition of which are different from each other, were synthesized by controlling hydrothermal synthesis time under the same synthesis conditions, dewaxing catalysts were fabricated using these EU-2 zeolites and then the isomerization performances thereof were compared with each other, the isomerization performance of the phase-transited EU-2 zeolite such as cristobalite, quartz or the like was excellent compared to that of pure EU-2 zeolite. Further, the present researchers found that, even when EU-2 zeolites were synthesized by changing the synthesis condition such as ratio of silica and aluminum or the like, the isomerization performance of the phase-transited EU-2 zeolite was excellent compared to that of pure EU-2 zeolite. The present invention is based on these findings.

The purity of the zeolite material itself and whether the material created by the phase transition of the zeolite material exists are evaluated by X-ray diffraction (XRD) analysis. Here, the relative amounts of created materials may be compared by comparing the characteristic XRD peaks of the materials with each other. XRD analysis is usefully used to grasp the degree of phase transition of EU-2 zeolite because the XRD peaks of cristobalite, quartz or the like can be observed in addition to the XRD peaks of EU-2 zeolite.

FIG. 1 shows the XRD peaks of the EU-2 zeolite obtained according to the following zeolite synthesis condition of Example 1. In FIG. 1, the XRD peaks (20) of EU-2 zeolite appear at 21.0° and 23.0°, the XRD peak of cristobalite appears at 22.0°, and the XRD peak of quartz appear at 26.5°. Therefore, it can be ascertained from FIG. 1 that EU-2 zeolite having high crystal purity is phase-transited into cristobalite and quartz with the passage of synthesis time, and that quartz is highly developed when synthesis time further increases.

Figure 2:
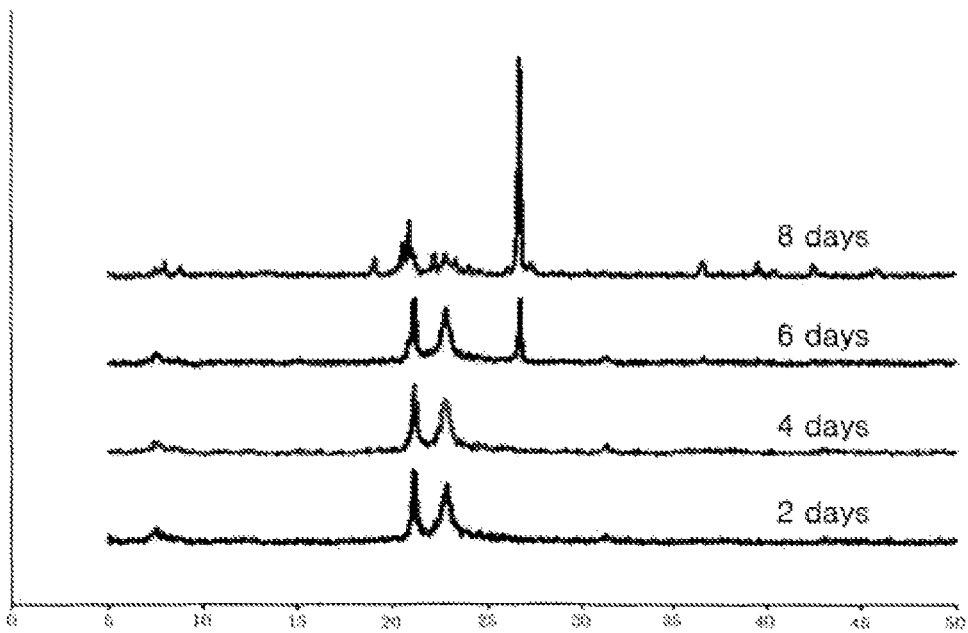
FIG. 2 is a view showing the X-ray diffraction (XRD) patterns of a hydrothermally-synthesized pure EU-2 zeolite material and an EU-2 zeolite material phase-transited with the passage of synthesis time.

FIG. 2 shows the XRD peaks of the EU-2 zeolite obtained according to the following zeolite synthesis condition of Example 4. From FIG. 2, similarly to FIG. 1, it can be ascertained that pure EU-2 zeolite is converted into different phases with the increase of synthesis time. However, From FIG. 2, differently from FIG. 1, it can be ascertained that the phase transition of EU-2 zeolite into cristobalite is not observed, and the phase transition of EU-2 zeolite into quartz rapidly proceeds from the beginning. Therefore, it can be ascertained that the tendency and speed of phase transition can be somewhat changed depending on the change of synthesis conditions.

The present researchers have attempted to numerically express the degree of phase transition of EU-2 zeolite and compare them. However, it was difficult to determine the degree of phase transition thereof because the degree of phase transition of a modified material was not able to be easily distinguished by XRD peaks when the content thereof is low, and because the sensitivity of materials to XRD is different with respect to each material. Therefore, the present researchers used thermogravimetric analysis (TGA) as a method of determining the degree of phase transition of EU-2 zeolite in combination with XRD analysis. Since the EU-2 before calcination after hydrothermal reaction (hereinafter referred to as "synthesized EU-2") includes an organic template material, when it is heated to a high temperature using TGA, the organic template material is decomposed and removed, thus reducing the weight of the synthesized EU-2. Generally, in the TGA analysis of zeolite before calcination, the weight of zeolite crystals including a large amount of a template material is greatly reduced, and the weight of zeolite crystals including a small amount of a template material is slightly reduced. Meanwhile, it was found that the degree of phase transition of EU-2 can be quantified by TGA analysis as the phase transition of EU-2 proceeds. That is, a sample was obtained by synthesizing pure EU-2 zeolite having high crystal purity for 48 hours (2 days) and the relative weight reduction of the sample was grasped, thus quantitatively evaluating the degree of phase transition of EU-2 zeolite. Based on the evaluation thereof, an EU-2 phase transition index is defined as follows.

EU-2 phase transition index (briefly, "T")[1]=(TGA weight reduction rate of the synthesized EU-2 sample[2])/(TGA weight reduction rate of pure EU-2 reference sample[3])×100

1) Index representing the degree of phase transition of a synthesized EU-2 sample according to the change of synthesis time under a predetermined EU-2 synthesis condition.

2) TGA analysis condition: TGA weight reduction rate of a synthesized EU-2 sample, which is measured under the condition that the sample is heated from 120° C. to 550° C. at a heating rate of 2° C./min and then maintained at 550° C. for 2 hours.

3) TGA weight reduction rate of a pure EU-2 sample synthesized for 48 hours, which is measured in the same manner as 2) under a predetermined synthesis condition.

In other words, it was found that, as a result of TGA analysis of EU-2 zeolites synthesized under the condition of synthesis time being different, the TGA weight reduction rate thereof decreases when the phase transition of EU-2 zeolite proceeds, that is, when the synthesis time thereof increases. The results of the TGA weight reduction rate of the obtained EU-2 zeolite according to synthesis time under the same synthesis condition are shown in Table 1 below. From FIGS. 1 and 2, it can be ascertained that the degree of phase transition of EU-2 zeolite, observed by XRD peak, corresponds to the degree of the TGA weight reduction rate thereof.

TABLE 1

| Synthesis time (day) | Synthesis condition of FIG. 1 | | Synthesis condition of FIG. 2 | |
|---|---|---|---|---|
| | TGA weight reduction rate (%) | EU-2 phase transition index (T) | TGA weight reduction rate (%) | EU-2 phase transition index (T) |
| 2 | 8.6 | 100.0 | 8.6 | 100.0 |
| 4 | 8.0 | 93.0 | 8.5 | 98.8 |
| 6 | 7.2 | 83.7 | 7.8 | 90.7 |
| 8 | 5.2 | 60.5 | 4.8 | 55.8 |
| 21 | 4.1 | 47.7 | | |

Therefore, from the fact that the TGA weight reduction rate of EU-2 zeolite decreases according to the degree of phase transition thereof, the degree of phase transition of EU-2 zeolite can be quantitatively evaluated from the relative TGA weight reduction rate of EU-2 zeolite based on the EU-2 sample having the highest crystal purity, and thus the EU-2 phase transition index is defined as above. Meanwhile, it must be cautioned that phase transition indexes are not absolutely matched with each other because they are changed according to the synthesis condition although they decrease in proportion to synthesis time.

Accordingly, the method of manufacturing a catalyst for an isomerization catalyst includes the steps of: mixing a template material with an aqueous alkali solution including a silica raw material and an alumina raw material; and hydrothermally synthesizing the mixture at a reaction temperature of 50° C. or more, preferably 50∞250° C., and more preferably 100~200° C. to obtain an EU-2 zeolite, the degree of phase transition of which is controlled such that the phase transition index (T) thereof is 50≤T<100.

The template material may be at least one selected from the group consisting of organic nitrogen-containing compounds, such as alkyl amines, tetramethyl ammonium compounds and di-quaternary ammonium compounds. The silica raw material may be at least one selected from the group consisting of silica sol, fumed silica, aerosil and tetraorthosilicate. Further, the silica material may be a silica sol such as Ludox HS-40 or Ludox AS-30. The alumina raw material may be at least one selected from the group consisting of sodium aluminate, aluminum nitrate, aluminum sulfate, $AlCl_3$, $Al(OH)_3$ and $Al(OCH_3)_3$.

The hydrothermal synthesis may be performed in an alkaline state of pH of 9 or more, preferably pH of 12 or more. The time it takes to conduct the hydrothermal synthesis is related to reaction temperature or stirring conditions. Preferably, the hydrothermal synthesis time may be 1 hour or more. The synthesis time can be controlled according to the phase transition index of the obtained EU-2 zeolite.

Figure 4:
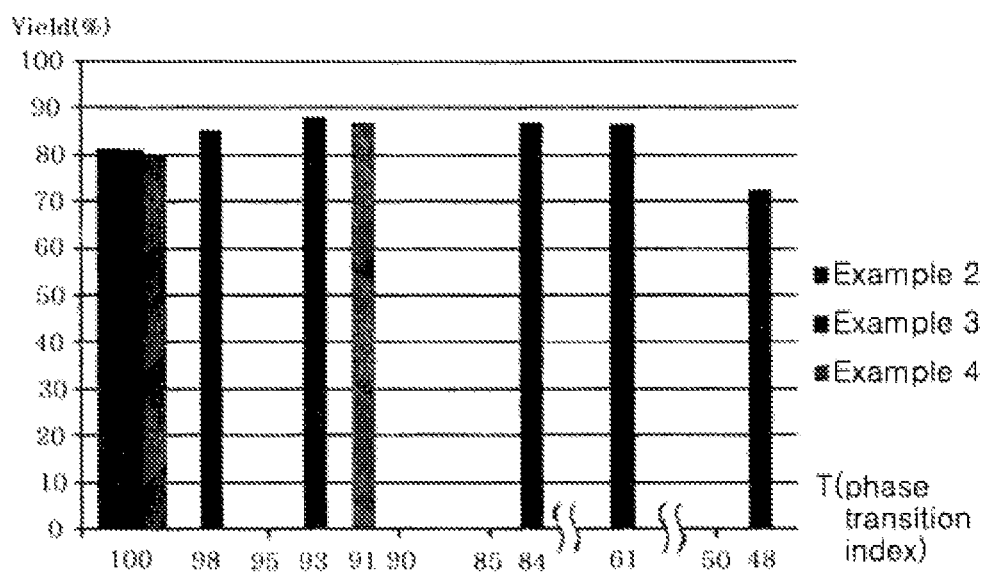
FIG. 4 is a graph showing the relationship of an isomerization yield to a phase transition index according to an embodiment of the present invention.

The phase transition index (T) of EU-2 zeolite may be EU-2 zeolite, 50≤T<100, preferably 60≤T<100, and more preferably 60≤T<98 as shown in FIG. 4. When the phase transition index (T) thereof is less than 50 or more than 100, an impurity such as cristobalite or quartz is not included in the EU-2 zeolite to such a degree that it does not influence the improvement of isomerization efficiency, or is excessively included in the EU-2 zeolite to such a degree that isomerization efficiency decreases.

In an embodiment of the present invention, the method of manufacturing a catalyst for an isomerization catalyst may further include the step of washing and drying the phase transition-controlled EU-2 zeolite.

In order to provide an acid property to the phase transition-controlled EU-2 zeolite support, the phase transition-controlled EU-2 zeolite support may be calcinated at a temperature of 500° C. or more and then ion-exchanged with cations such as $NH^{4+}$ or the like.

The molar ratio of silica and alumina in the phase transition-controlled EU-2 zeolite support may be 1~500, preferably 20~200. The BET surface area of the phase transition-controlled EU-2 zeolite support may be 100 $m^2/gr$ or more.

The method of manufacturing a catalyst for an isomerization catalyst may further include the steps of loading a active metal composition on the synthesized EU-2 zeolite support for hydrogenation, and drying and calcinating the resultant product. The catalyst manufactured using this method is a catalyst for an hydroisomerization reaction, in which an EU-2 zeolite support, the degree of phase transition of which is controlled such that its phase transition index (T) is 50~100 based on the reference EU-2 phase transition index proposed by the present researchers, is loaded with a metal composition for hydrogenation. The bifunctional catalyst according to the present invention is used as a catalyst for a hydrodewaxing process.

In the bifunctional catalyst according to the present invention, an EU-2 zeolite support, the degree of phase transition of which is controlled, may be used as a catalyst support having an acid site, and an oxide, such as alumina, silica or the like, may be used as a binder. The metal for hydrogenation may be at least one selected from the group consisting of group VI metals and group VIII metals. Preferably, the metal for hydrogenation may be a precious metal such as platinum or palladium.

In order to manufacture the catalyst for an isomerization reaction, the ion-exchanged EU-2 zeolite, the phase transition of which is controlled, may be loaded with at least one selected from the group consisting of group VI metals and group VIII metals, and preferably, may be loaded with a precious metal such as platinum or palladium. The method of loading a metal on an EU-2 zeolite support can be conducted using impregnation, ion exchange or the like.

In this case, in order to improve the selectivity of the catalyst to an isomerization reaction, at least one selected from the group consisting of group I metals and group II metals may be added as a co-catalyst. Examples of the group I metals and group II metals may include sodium, magnesium and calcium.

Subsequently, the EU-2 zeolite support loaded with the metal is shaped, dried and then calcinated to manufacture the catalyst of the present invention. Here, the calcination of the EU-2 zeolite support is generally carried out at 350~600° C. for 1~24 hours.

Meanwhile, in order to activate and pre-treat the catalyst, drying, reduction, pre-sulfidation or the like may be required, and, if necessary, may be omitted or changed.

The catalyst manufactured using this method can be used as a catalyst for a hydrodewaxing process under the reaction conditions of a temperature of 250~420° C., a hydrogen partial pressure of 1~200 atm, a liquid hourly space velocity of 0.1~10 $h^{-1}$ and a hydrogen treatment rate of 45~1780 $m^3/m^3$ (250~10,000 scf/B).

MODE FOR INVENTION

Hereinafter, the present invention will be described in more detail with reference to the following examples. However, the scope of the present invention is not limited to these examples. The general method of synthesizing EU-2 zeolite, used in the present invention, may refer to the method disclosed in U.S. Pat. No. 4,741,891.

Example 1

9.8 g of hexamethonium chloride as a template material, 2.8 g of sodium aluminate as an alumina raw material, 203.6 g of Ludox-HS40 as a silica raw material and 10.4 g of sodium hydroxide (NaOH) were dissolved in 292 g of DI water to form a mixed solution. Subsequently, the mixed solution was put into a hydrothermal reactor coated with Teflon, and then reacted at 165° C. for 2 days (48 hours) to obtain a zeolite material. Subsequently, the zeolite material was sufficiently washed with distilled water, dried at 60° C. for 12 hours, and then calcinated at 550° C. for 5 hours. Here, the zeolite material obtained in this way is zeolite having only a pure EU-2 crystal structure, which was disclosed in the Patent document.

The hydrothermally-synthesized EU-2 zeolite was ion-exchanged with $NH^{4+}$ using a 1N aqueous ammonium nitrate solution. The ion-exchanged EU-2 zeolite was mixed with psuedoboemite as a binder at a mixing ratio of 1:1. Then, the mixture of the EU-2 zeolite and the binder was impregnated with an aqueous $H_2PtCl_6$ solution such that the amount of the EU-2 zeolite was 0.6 wt % based on the content of Pt. The impregnated EU-2 zeolite was dried at 120° C. for 3 hours, and then calcinated at 500° C. for 3 hours to manufacture a catalyst for an isomerization reaction.

Another catalyst was manufactured in the same manner as above, except that the synthesis reaction time was changed to 4 days (96 hours). In this case, as the result of XRD analysis of the material obtained in this process, the material was a metal including EU-2 and cristobalite.

The XRD patterns of the obtained material are shown in the synthesis reaction time (2 days, 4 days) of FIG. 1. When the synthesis reaction time was 2 days, it can be seen that the material is pure EU-2 zeolite having a specific peak. When the synthesis reaction time was 4 days, it can be seen that EU-2 zeolite crystal is phase-transformed, thus observing the specific peaks of cristobalite and quartz.

The reaction test of n-hexadecane was carried out using two kinds of the obtained catalyst for an hydroisomerization reaction.

The test started after filling a fixed-bed reactor having an outer diameter of half an inch with the obtained catalyst for an isomerization reaction and then activating the catalyst at 260° C. for 1 hour or more. In the test, n-hexadecane was introduced into the reactor at a feed rate of 1 g/hr using a pump, reaction pressure was 30 atm, and hydrogen was introduced into the reactor at a flow rate of 650 cc/hr. In this case, the conversion ratio of n-hexadecane can be controlled by controlling reaction temperature, and both the selectivity of the catalyst to a cracking reaction and the selectivity of the catalyst to an isomerization reaction were changed according to the change in the conversion ratio of n-hexadecane. In the test, the conversion ratio of n-hexadecane was changed according to the change of reaction temperature, and the selectivity of the catalyst to a cracking reaction and the selectivity of the catalyst to an isomerization reaction under the same conversion ratio were different according to the change of catalyst, so that the yields of iso-hexadecane, obtained by GC analysis, were different by different cataylsts. When the concentration of iso-hexadecane, among the reaction products obtained according to various reaction temperatures, was highest, this was defined by the maximum yield of isomerization reaction product using the catalyst.

Figure 3:
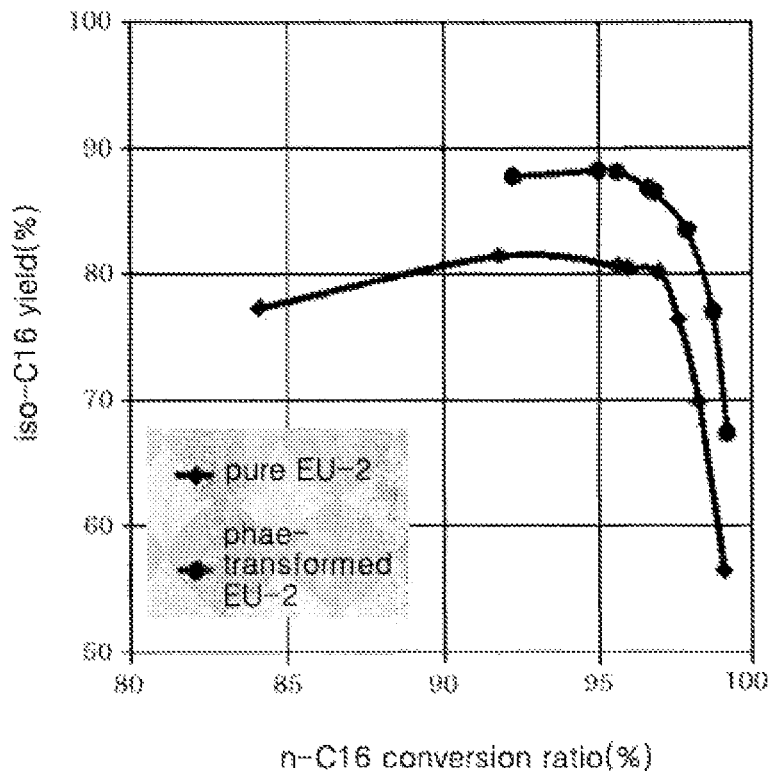
FIG. 3 is a graph showing the function of iso-C16 yield to n-C16 conversion ratio.

The test results of the isomerization reaction of n-hexadecane using the two kinds of catalysts are shown in FIG. 3. As shown in FIG. 3, it can be ascertained that the selectivity to an isomerization reaction and the yield of iso-hexadecane of the catalyst manufactured using the phase-transformed EU-2 zeolite are improved compared to those of the catalyst manufactured using pure EU-2 zeolite.

Example 2

Example 2 was carried out in the same manner as in Example 1, except that the synthesis reaction time was changed. The phase transition index of the phase-transformed EU-2 zeolite and the maximum yield of the isomerization reaction product obtained in the reaction test of n-hexadecane using the catalyst manufactured using the same are shown in Table 2. The process of manufacturing the catalyst and the reaction test of n-hexadecane were carried out in the same manner as in Example 1.

TABLE 2

| Synthesis reaction time (days) | XRD peak | EU-2 phase transition index (T) | Maximum yield (%) |
| --- | --- | --- | --- |
| 2 | Pure EU-2 (Comp. Exp.) | 100.0 | 81.6 |
| 4 | Phase-transformed EU-2 (Exp. 1) | 93.0 | 88.3 |
| 6 | Phase-transformed EU-2 | 83.7 | 87.0 |
| 8 | Phase-transformed EU-2 | 60.5 | 86.4 |
| 21 | Phase-transformed EU-2 | 47.7 | 72.5 |

The results of carrying out an isomerization reaction test using the EU-2 zeolite having the above phase transition index (T) as a support of a catalyst for an isomerization reaction are as follows. When the phase transition index (T) is 60~100, preferably 60~98, the yield of isomerization reaction becomes a maximum yield, and thereafter, as the phase transition index (T), decreases, the yield of isomerization reaction slightly decreases with respect to the maximum yield. Further, when the phase transition index (T) (synthesis reaction time: 21 days) is 50 or less, the yield of isomerization reaction of the phase-transformed EU-2 zeolite decreases compared to the yield of the isomerization reaction of pure EU-2 zeolite.

Example 3

9.8 g of hexamethonium chloride as a template material, 2.35 g of sodium aluminate as an alumina raw material, 203.6 g of Ludox-HS40 as a silica raw material and 10.8 g of sodium hydroxide (NaOH) were dissolved in 292 g of DI water to form a mixed solution. Subsequently, the mixed solution was put into a hydrothermal reactor coated with Teflon, and then reacted under the same synthesis conditions as in Example 1 to obtain a phase-transformed EU-2 zeolite material. The phase transition index of the obtained phase-transformed EU-2 zeolite material and the results of carrying out the reaction test of n-hexadecane using the catalyst manufactured using the same are shown in Table 3 below. The process of manufacturing the catalyst and the reaction test of n-hexadecane were carried out in the same manner as in Example 1.

TABLE 3

| Synthesis reaction time (days) | XRD peak | EU-2 phase transition index (T) | Maximum yield (%) |
| --- | --- | --- | --- |
| 2 | Pure EU-2 | 100.0 | 81.3 |
| 4 | Phase-transformed EU-2 | 97.6 | 85.2 |

As shown in Table 3 above, it can be ascertained that, when the phase-transformed EU-2 zeolite having a phase transition index (T) of 97.6 is used as a catalyst support of a catalyst for an isomerization reaction, the yield of the isomerization reaction of the phase-transformed EU-2 zeolite is improved compared to the yield of an isomerization reaction of pure EU-2 zeolite.

Example 4

12.8 g of hexamethonium chloride as a template material, 4.95 g of sodium aluminate as an alumina raw material, 264.7 g of Ludox-HS40 as a silica raw material and 13.5 g of sodium hydroxide (NaOH) were dissolved in 260 g of DI water to form a mixed solution. Subsequently, the mixed solution was put into a hydrothermal reactor coated with Teflon, and then reacted under the same synthesis conditions as in Example 1 to obtain a phase-transformed EU-2 zeolite material. The phase transition index of the obtained phase-transformed EU-2 zeolite material and the results of carrying out the reaction test of n-hexadecane using the catalyst manufactured using the same are shown in Table 4 below. The process of manufacturing the catalyst and the reaction test of n-hexadecane were carried out in the same manner as in Example 1.

TABLE 4

| Synthesis reaction time (days) | XRD peak | EU-2 phase transition index (T) | Maximum yield (%) |
| --- | --- | --- | --- |
| 2 | Pure EU-2 | 100.0 | 80.6 |
| 6 | Phase-transformed EU-2 | 90.7 | 86.8 |

As shown in Table 4 above, it can be ascertained that, when the phase-transformed EU-2 zeolite having a phase transition index (T) of 90.7 is used as a catalyst support of a catalyst for an isomerization reaction, the yield of the isomerization reaction of the phase-transformed EU-2 zeolite is improved compared to the yield of an isomerization reaction of pure EU-2 zeolite.

Example 5

A pilot test was carried out in order to ascertain the fact that the catalyst manufactured using the phase-transformed EU-2 zeolite obtained in Example 1 under the synthesis condition of a synthesis reaction time of 4 days as a catalyst support can be used to prepare a raw material of a lubricant using a hydrocarbon having a high boiling point.

The manufactured catalyst accelerated the hydrodewaxing reaction of a feed having a pour point of 48° C. under the reaction conditions of a temperature of 340° C., a hydrogen partial pressure of 144 atm, a liquid hourly space velocity of 1 h$^{-1}$ and a hydrogen treatment rate of 550 m$^3$/m$^3$ to obtain a 310+C product having an improved pour point of −14° C. In this case, since the catalyst suppresses a cracking reaction and increases its selectivity to an isomerization reaction, the yield loss caused by the cracking reaction was 9% or less. The properties of the feed and product used in the pilot test are given in Table 5.

TABLE 5

|  | Feed | Product |
|---|---|---|
| API | 35.8 |  |
| Specific gravity | 0.8458 | 0.834 |
| Distillation, D2887 |  |  |
| 10% | 394.6 |  |
| 90% | 451.0 |  |
| Sulfur, wtppm | 4.6 | <1.0 |
| Nitrogen, wtppm | 2.0 | <1.0 |
| Kinematic viscosity@40° C., cSt | 35.1 | 35.88 |
| Kinematic viscosity@100° C., cSt | 6.543 | 6.429 |
| Viscosity index | 143 | 132 |
| PP, ° C. | 48 | −14 |

The invention claimed is:

1. A hydrodewaxing method of a hydrocarbon raw material, wherein the hydrocarbon raw material is hydrodewaxed in the presence of a catalyst under the reaction conditions of a temperature of 250~420° C., a hydrogen partial pressure of 1~200 atm, a liquid hourly space velocity of 0.1~10 h$^{-1}$ and a hydrogen treatment rate of 250~10,000 scf/B, wherein the catalyst comprises an EU-2 zeolite support having an acid site, the phase transition index (T) thereof, represented by Formula 1 below, being 60≤T<98, and the molar ratio of silica and alumina thereof being 20 to 200; and a metal composition for hydrogenation loaded in the EU-2 zeolite support, the metal composition including at least one metal selected from the group consisting of group VI metals and group VIII metals, wherein <Formula 1> T=(TGA weight reduction rate of the synthesized EU-2 sample)/(TGA weight reduction rate of pure EU-2 reference sample)×100 (here, the TGA weight reduction rate of the EU-2 sample is measured under the condition that the sample is heated from 120° C. to 550° C. at a heating rate of 2° C./min and then maintained at 550° C. for 2 hours).

2. The hydrodewaxing method of a hydrocarbon raw material according to claim 1, wherein the metal composition is palladium or platinum.

3. The hydrodewaxing method of a hydrocarbon raw material according to claim 1, wherein the catalyst further comprises at least one co-catalyst selected from the group consisting of group I metals and group II metals.

4. The hydrodewaxing method of a hydrocarbon raw material according to claim 3, wherein each of the group I metals and group II metals is selected from sodium, magnesium and calcium.

5. A hydrodewaxing method of a hydrocarbon raw material, wherein the hydrocarbon raw material is hydrodewaxed in the presence of a catalyst under the reaction conditions of a temperature of 250~420° C., a hydrogen partial pressure of 1~200 atm, a liquid hourly space velocity of 0.1~10 h$^{-1}$ and a hydrogen treatment rate of 250~10,000 scf/B, wherein the catalyst is prepared by the steps of:

(a) preparing an EU-2 zeolite support, the degree of phase transition of which is controlled such that a phase transition index (T) thereof is 60≤T<98;

(b) loading a active metal composition on the EU-2 zeolite support for hydrogenation, the metal composition including at least one metal selected from the group consisting of group VI metals and group VIII metals; and (c) drying and calcinating the EU-2 zeolite support loaded with the metal composition, wherein T=(TGA weight reduction rate of the synthesized EU-2 sample)/(TGA weight reduction rate of pure EU-2 reference sample)× 100 (here, the TGA weight reduction rate of the EU-2 sample is measured under the condition that the sample is heated from 120° C. to 550° C. at a heating rate of 2° C./min and then maintained at 550° C. for 2 hours).

6. The hydrodewaxing method of a hydrocarbon raw material according to claim 5, wherein the step (a) comprises the steps of: (i) mixing a template material with an aqueous alkali solution including a silica raw material and an alumina raw material; (ii) reacting the mixture at a temperature of 50~250° C. to obtain an EU-2 zeolite, the degree of phase transition of which is controlled such that the phase transition index (T) thereof is 60≤T<98; and (iii) washing and drying the EU-2 zeolite.

7. The hydrodewaxing method of a hydrocarbon raw material according to claim 6, wherein the template material is at least one member selected from the group consisting of alkyl amines, tetramethyl ammonium compounds and di-quaternary ammonium compounds.

8. The hydrodewaxing method of a hydrocarbon raw material according to claim 5, wherein the step (b) further comprises the step of adding at least one co-catalyst selected from the group consisting of group I metals and group II metals.

9. The hydrodewaxing method of a hydrocarbon raw material according to claim 8, wherein each of the group I metals and group II metals is selected from sodium, magnesium and calcium.

* * * * *